(12) United States Patent
Bödiger et al.

(10) Patent No.: US 6,723,881 B1
(45) Date of Patent: Apr. 20, 2004

(54) METHOD FOR CONDITIONING ION EXCHANGERS

(75) Inventors: Michael Bödiger, League City, TX (US); Rainer Neumann, Krefeld (DE); Frieder Heydenreich, Düsseldorf (DE); Michael Prein, Brasschaat (BE); Gerhard Fennhoff, Willich (DE); Ulrich Schnegg, Leverkusen (DE); Rudolf Wagner, Köln (DE); Wolfgang Wambach, Köln (DE); Reinhold Klipper, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/130,373

(22) PCT Filed: Nov. 16, 2000

(86) PCT No.: PCT/EP00/11352

§ 371 (c)(1),
(2), (4) Date: Aug. 28, 2002

(87) PCT Pub. No.: WO01/37992

PCT Pub. Date: May 31, 2001

(30) Foreign Application Priority Data

| Nov. 23, 1999 | (DE) | ......................................... 199 56 229 |
| Jun. 6, 2000 | (DE) | ......................................... 100 27 908 |

(51) Int. Cl.[7] ............................................. C07C 39/12
(52) U.S. Cl. ...................................... 568/168; 502/109
(58) Field of Search ........................... 568/728; 502/159

(56) References Cited

U.S. PATENT DOCUMENTS

| 3,037,052 A | | 5/1962 | Bortnick ...................... 260/485 |
| 4,191,843 A | | 3/1980 | Kwantes et al. ............. 568/728 |
| 4,365,099 A | * | 12/1982 | Faler |
| 4,444,961 A | | 4/1984 | Timm ........................... 526/88 |
| 5,146,007 A | | 9/1992 | Cipullo ....................... 568/727 |
| 5,233,096 A | | 8/1993 | Lundquist .................... 568/727 |
| 5,324,867 A | * | 6/1994 | Asaoka |
| 5,502,016 A | | 3/1996 | Kiedik et al. .................. 502/11 |
| 5,648,561 A | * | 7/1997 | Minhua |
| 5,696,295 A | * | 12/1997 | Wulff |
| 5,723,691 A | * | 3/1998 | Cipullo |
| 6,417,318 B1 | * | 7/2002 | Heydenreich |
| 6,590,128 B1 | * | 7/2003 | Bodiger |

FOREIGN PATENT DOCUMENTS

| DE | 198 52 667 | | 5/2000 |
| EP | 0 765 685 | | 4/1994 |
| JP | 6-340564 | * | 12/1994 |

OTHER PUBLICATIONS

Zeitschrift für Physik. Chemie Neue Folge, (Frankfurt), Bd. 59, pp. 225–241 (month unavailable) 1968, G. Zundel und H. Metzger, Die Hydratation der Polystyrol–Sulfonsäure, eine IR–spektrosko–pische Untersuchung.

* cited by examiner

Primary Examiner—Michael L. Shippen
(74) Attorney, Agent, or Firm—Joseph C. Gil; Jennifer R. Seng; John E. Mrozinski, Jr.

(57) ABSTRACT

Monodisperse cation-exchangers and anon-exchangers are conditioned by a process and thereafter used as catalysts and for the production of bisphenols.

Figure 1:
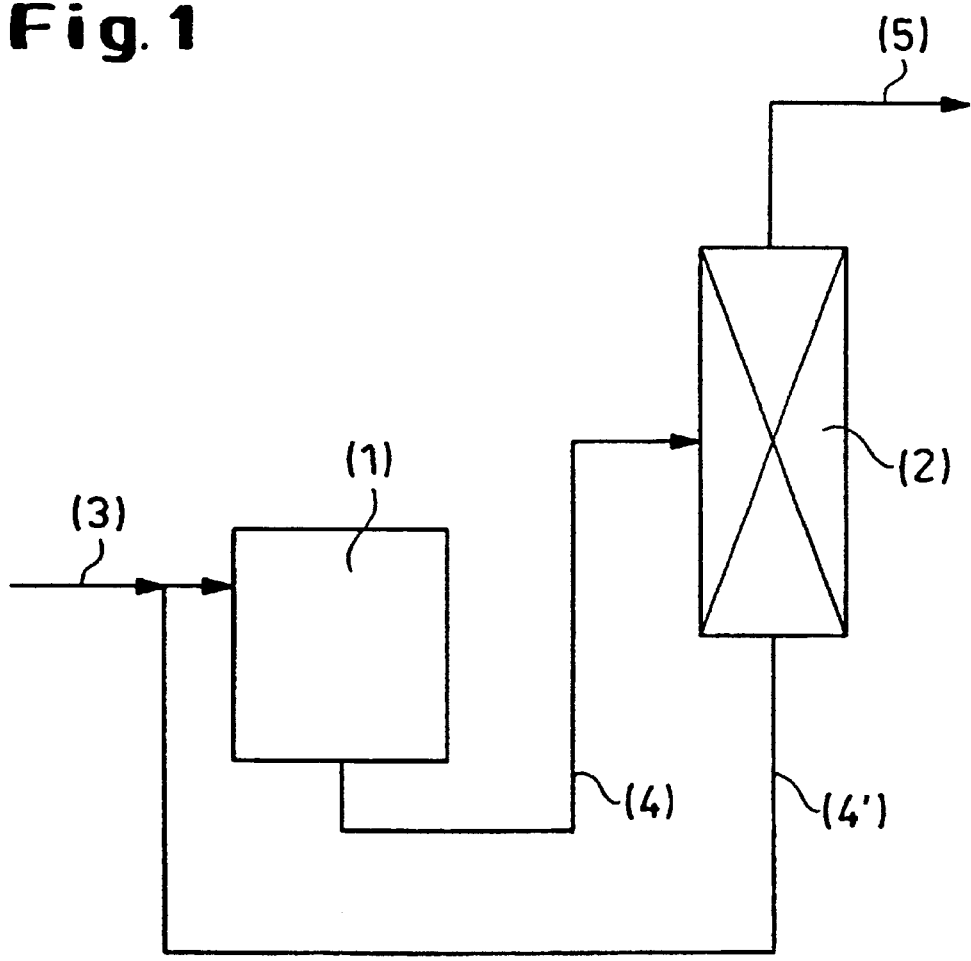

8 Claims, 1 Drawing Sheet

METHOD FOR CONDITIONING ION EXCHANGERS

FIELD OF THE INVENTION

This application relates to the conditioning and use of ion-exchangers for the production of bisphenols.

The present application relates, in particular, to the conditioning of monodisperse cation-exchangers and anion-exchangers and also to the use thereof as catalysts, in particular for the catalysis of condensation reactions.

BACKGROUND OF THE INVENTION

Condensation reactions, such as the synthesis of bisphenols, for example, which is generally undertaken by acid-catalysed conversion of phenols with carbonyl compounds, are known from the literature. The latter reaction is generally carried out in fixed-bed or fluidised-bed reactors, as well as in reagent columns.

For example, catalysts consisting of cross-linked sulfonated polystyrene resins (acidic ion-exchangers) are conventionally used in the synthesis of bisphenols.

These ion-exchangers may optionally be chemically modified by covalently or ionically bonded co-catalysts and are macroporous or gel-like (U.S. Pat. Nos. 4,191,843; 3,037,052). According to U.S. Pat. No. 5,233,096, jetted suspension-polymerised styrene copolymers that have been functionalised with strongly acidic functional groups are employed for the condensation reaction of phenol with aldehydes or ketones to form bisphenols.

In the commercial form the ion-exchangers contain 45 to 85 wt. % water. In order to avoid a competition of water relative to the feed materials at the catalytic points and consequently to avoid a decrease in the activity of the ion-exchanger, for use in the course of the production of technically important 2,2-bis(4-hydroxyphenyl)propane (BPA), for example, the water should be largely removed. Furthermore, by reason of their production process, standard commercial ion-exchangers are provided with certain amounts of acidic oligomer portions which, in the case of continuous flow, can be washed out with reaction solution and have a negative influence on the purity, thermostability and colour of products that are prepared with them.

With a view to improving the space-time yields and with a view to increasing the selectivities of production processes in which these ion-exchangers are employed as catalysts it is therefore necessary to condition the catalyst prior to initial use.

It is therefore an object of the present invention to condition ion-exchangers based on cross-linked sulfonated polystyrene resins in such a way that a contamination of the reaction product with acidic fragments in the course of condensation reactions is prevented. In the case of the synthesis of bisphenols which has already been described above, trouble-free starting with phenol/acetone mixtures is consequently to be guaranteed without activation losses occurring in the course of the transfer of the ion-exchanger which has been conditioned in this way into the reaction vessel and that the flows of material arising in the course of conditioning can be processed meaningfully and can optionally be recycled without unnecessary loss of material occurring.

In the case of the synthesis of bisphenols, various attempts to achieve this object have been described in the literature. For instance, a hydrous ion-exchanger can be dehydrated in the reaction vessel by rinsing with phenol, in which case water is entrained by flowing phenol. In this case a shrinkage of the ion-exchanger occurs which leads to an additional mechanical loading of the ion-exchanger and can consequently result in fracture of the grains. In addition, traces of oligomer are only removed inadequately with this procedure. Furthermore, this process is timeconsuming and the reaction vessel is not available for production during this period.

In U.S. Pat. No. 3,037,052 it is therefore recommended to dry the ion-exchanger at elevated temperatures (about 150° C.) prior to use for the synthesis of bisphenols. In this case, however, the rate of drying has to be controlled very precisely (cf. Zundel et al.

Physik. Chem. (Frankfurt), 59, 225 (1968)) and there is a risk of mechanical damage at the high temperatures.

The partial dehydration of the catalyst prior to decanting into the reactor is described in U.S. Pat. No. 5,146,007. 20 to 90% of the water is removed by vacuum drying or drying with a stream of carrier gas. Subsequently the catalyst is transferred into the reactor, and the residual water is removed by rinsing with phenol. With a procedure of this type, however, harmful water-soluble oligomer portions are not adequately removed. In EP-A-765 685 it is proposed firstly to wash the catalyst with water until a defined residual conductivity is attained, then to remove a part of the water by vacuum drying or carrier-gas drying and subsequently to reduce the water content down to <1% by continuous rinsing with phenol. Whilst this procedure provides for a separation of oligomer constituents, in practical implementation it is laborious, since special devices are necessary for the partial removal of water by vacuum technology or carrier-gas technology. Furthermore, large quantities of water and phenol accumulate which are contaminated with harmful catalyst constituents and cannot readily be returned to the process. In the case where washing with water and dehydration are implemented in the reactor container, production stoppages arise as a result of blockage of the container for the stated conditioning tasks.

In order to circumvent the disadvantages, described above, of the various conditioning processes, an integrated process for preparation of the catalyst is being developed that is suitable for the conditioning of ion-exchangers that are to be employed in condensation reactions.

DETAILED DESCRIPTION OF THE INVENTION

The application therefore provides a process for conditioning ion-exchangers, said process being characterised in that a) the ion-exchanger which has been moistened with water is suspended in a unit (1) with oxygen-free, completely de-ionized water at 5 to 80° C., in particular 20 to 60° C., whereby in particular a volume ratio of 3 to 1.5 parts, preferably 2.5 to 2 parts, of ion-exchanger which has been moistened with water to 1 part of water is adjusted and whereby the content of dissolved oxygen in the completely de-ionized water which is employed is preferably no greater than 1 ppm, preferably no greater than 100 ppb, and whereby the content of dissolved or undissolved metallic ions in the completely de-ionized water which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

b) the suspension is agitated, preferably by stirring for between half an hour and 24 hours at 5 to 80° C., in particular 20 to 60° C., and subsequently an analysis of the supernatant aqueous solution in respect of its conductivity is carried out, in order to obtain an indication of the oligomer content of the ion-exchanger and the number of necessary washing cycles for step c);

c) the ion-exchanger is subjected to discontinuous washing with oxygen-free, completely de-ionized water until constant residual conductivity is attained; washing is effected preferably 5 to 50 times, in particular 10 to 25 times, depending on the conductivity, whereby, after discharge of the completely deionized water, in each instance 0.2 to 1.5 parts by volume of completely deionized water, relative to the ion-exchanger which has been moistened with water, are added, the mixture is agitated and the completely de-ionized water is discharged and the conductivity of the completely de-ionized water is examined at the outlet, whereby the conductivity at the end of the washing cycles is less than 100 microSiemens/cm, preferably less than 50 microSiemens/cm, in particularly preferred manner less than 20 microSiemens/cm, and whereby the content of dissolved oxygen in the completely de-ionized water which is employed is preferably no greater than 1 ppm, preferably no greater than 100 ppb, and whereby the content of dissolved or undissolved metallic ions in the completely de-ionized water which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

d) after the final wash the completely de-ionized water is discharged, and oxygen-free phenol is admixed to the ion-exchanger at 50 to 90° C., in particular 60 to 80° C., whereby a volume ratio of 0.60 to 1.5 parts of ion-exchanger which has been moistened with water to one part of phenol is preferably adjusted and whereby the content of dissolved oxygen in the phenol which is used is preferably less than 1 ppm, preferably less than 100 ppb, and whereby the content of dissolved or undissolved metallic ions in the phenol which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

e) the existing mixture is dehydrated in a continuously operated circulating apparatus containing the unit (1) and at least one distillation unit (2) for the purpose of separating phenol and water, whereby the ion-exchanger which has been moistened with water is stirred in the unit (1), preferably under an inertgas atmosphere, with phenol at 50 to 90° C., preferably 60 to 80° C., and a partial flow of phenol of up to 20% of the total volume per hour is fed out via a pipe (4) and transferred into the distillation unit (2) and a separation into phenol (bottom product) and water/phenol mixture (top product) is carried out in the distillation unit (2) and the phenol is recycled into the unit (1) via pipe (4'). The phenolic water is preferably supplied to an extraction apparatus which is present in the production process. By way of distillation unit (2), in particular a distillation column which is optionally integrated within the production process is utilised for the purpose of separating water and phenol. The top product which is separated in this individual step contains 2 to 20 wt. %, preferably 5 to 10%, phenol. The phenol that is discharged from the system by this means is replenished in the unit (1) by means of fresh phenol. The mixture is conducted through the circulating apparatus until such time as a content of residual water at the outlet of the unit (1) of preferably less than 3 vol. %, preferably less than 1 vol. %, is measured;

f) the mixture is subsequently transferred in the form of a suspension consisting of ion-exchanger resin and phenol into a suitable reaction vessel, preferably under inert conditions, the suspension of ion-exchanger resin and phenol being present in pumpable form preferably at temperatures from 50 to 80° C. and preferably with a solids content from 40 to 80 vol. % and preferably g) the supernatant phenol is discharged from the reaction vessel.

The ion-exchanger that has been conditioned by this means is outstandingly suitable for the production of bisphenols, in particular for the production of BPA from acetone and phenol. The BPA that is produced with this ion-exchanger exhibits high product quality and is particularly suitable for the production of polymers such as epoxy resins and, in particular, polycarbonate.

The phenol that arises in the process according to the invention in the course of the conditioning of the ion-exchanger during g) is contaminated with acidic soluble portions stemming from the ion-exchanger. For arbitrary further use, in particular as initial material for the production of BPA, the phenol arising in this way is therefore optionally purified, preferably by distillation, the bottom of the column being charged with up to 5 wt. % of a basic compound that is suitable to retain acidic constituents. A preferred basic compound is sodium hydroxide.

An advantage of the process that has been described consists in the fact that, by this means, undesirable acidic oligomer portions are removed from the ion-exchanger (resulting, for example, in improved product quality). By virtue of the catalyst pretreatment in an external container, the production process can be continued in the reaction vessel during conditioning. The continuous dehydration of the catalyst with recycling of phenol requires a minimal quantity of phenol; no additional, technically sophisticated pieces of apparatus such as, for example, devices for vacuum drying or carrier-gas drying, are necessary. By virtue of the agitation of the suspension in the course of the dehydration, no mechanical stresses occur as a result of the diminution in volume of the particles of the ion-exchanger. Bypass flows arising can be processed in a production plant in which the ion-exchangers are employed as catalysts and in which distillation units and extraction units are present. In this connection the greater part of the phenol that is used for the purpose of dehydration can also be employed in the production process.

The BPA that is produced with such a catalyst resin exhibits high product quality and is especially suitable for the production of polymers such as epoxy resins and, in particular, polycarbonates. The polycarbonates that are produced in this way are used for the production of mouldings such as, in particular, compact discs, lenses and window panes.

The present application provides, moreover, a process for conditioning monodisperse ion-exchangers for the catalysis of condensation reactions, addition reactions, transesterifications or alkylation reactions, characterised in that a) monodisperse ion-exchangers which have been moistened with water are suspended in oxygen-free, completely de-ionized water, b) the monodisperse ion-exchanger is subjected to discontinuous or continuous washing with oxygen-free, completely de-ionized water until constant conductivity is attained, c) after the last wash the completely de-ionized water is discharged and the oxygen-free OH component is admixed to the monodisperse ion-exchanger, d) the mixture which is obtained is dehydrated in a continuously operated circulating apparatus with distillation unit and e) finally the suspension consisting of monodisperse ion-exchanger and OH component is transferred into a reaction vessel.

The present invention also provides the monodisperse ion-exchangers that have been conditioned for catalysis of the aforementioned reactions in accordance with process steps a) to e), both as cation-exchangers and as anion-exchangers.

According to the present invention, the phrase 'completely de-ionized water' means fully demineralized or desalinated water. Phenols, ortho-, meta-, para-cresols or α- or β-naphthols enter into consideration, for example, as possible OH components for condensation reactions in the sense of the present invention.

The monodisperse ion-exchangers to be conditioned in connection with the catalysis of the aforementioned reactions, in particular of condensation reactions according to the present application, exhibit microporous or gel-like or macroporous structures. These structures have been described in detail in the technical literature. With a view to catalysis of the aforementioned reactions, particularly of condensation reactions, however, macroporous or gel-like monodisperse ion-exchangers are preferably employed. According to the present invention, gel-like monodisperse ion-exchangers are employed in particularly preferred manner in the synthesis of BPA, for example.

The monodisperse ion-exchangers to be conditioned in accordance with the present invention for catalysis of the aforementioned reactions, particularly of condensation reactions, may be produced by known processes.

By way of example, monodisperse ion-exchangers are produced in accordance with U.S. Pat. No. 4,444,961 or DE-A 19 852 667.

Substances are designated as monodisperse ion-exchangers in the present application in which at least 90% by volume or by mass of the particles have a diameter that lies within the interval with a width of ±10% of the most frequent diameter around the most frequent diameter.

For example, in the case of a substance with most frequent diameter amounting to 0.5 mm, at least 90% by volume or by mass lies within a size interval between 0.45 mm and 0.55 mm; in the case of a substance with most frequent diameter amounting to 0.7 mm, at least 90% by volume or by mass lie within a size interval between 0.77 mm and 0.63 mm.

However, the process according to the invention for conditioning monodisperse ion-exchangers not only avoids the disadvantages, described above, of the known conditioning processes but at the same time enables optimal use of the conditioned monodisperse ion-exchangers as catalyst resins in condensation reactions, preferably in condensation reactions starting from phenols, o-, m-, p-cresols or α- or β-naphthols, in particularly preferred manner in the synthesis of bisphenols, in quite particularly preferred manner for synthesising BPA from phenols and aldehydes or ketones.

But the conditioned monodisperse ion-exchangers are also outstandingly suitable for use as catalysts in the case of addition reactions. As an example of an addition reaction, the addition of alcohols to alkenes may be mentioned, preferably of alcohols to $C_1$–$C_4$-alkenes, in particularly preferred manner of methanol, ethanol, propanol or butanol to isobutene, in quite particularly preferred manner of methanol to isobutene to form methyl-t-butyl ether.

The conditioned monodisperse ion-exchangers are suitable, in addition, for the catalysis of esterifications by reaction of alcohols with carboxylic acids, preferably of $C_1$–$C_8$-alcohols with $C_1$–$C_8$-carboxylic acids, in particularly preferred manner for the esterification of methanol, ethanol, propanol and all isomers of butanol with carboxylic acids pertaining to the series constituted by formic acid, acetic acid, propionic acid or butyric acid.

In addition, the conditioned monodisperse ion-exchangers are suitable for the catalysis of transesterification reactions, for example of triesters to form monoesters, in particular the transesterification of a triglyceride with methanol, ethanol, propanol or butanol to form a fatty-acid monoester.

Finally, the conditioned monodisperse ion-exchangers are suitable for the catalysis of alkylation reactions, for example the alkylation of phenols or cresols with linear or branched olefins, for example to form triisobutene or nonene.

The present application preferably provides a process for conditioning monodisperse ion-exchangers for the catalysis of condensation reactions, in particular the synthesis of bisphenols, characterised in that a) the monodisperse ion-exchanger which has been moistened with water is suspended in a unit (1) with oxygen-free, completely de-ionized water at 5 to 80° C., in particular 20 to 60° C., whereby in particular a volume ratio of 3 to 1.5 parts, preferably 2.5 to 2 parts, of ion-exchanger which has been moistened with water to 1 part of water is adjusted and whereby the content of dissolved oxygen in the completely de-ionized water which is employed is preferably no greater than 1 ppm, preferably no greater than 100 ppb, and whereby the content of dissolved or undissolved metallic ions in the completely de-ionized water which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

b) the suspension is agitated, preferably by stirring for between half an hour and 24 hours at 5 to 80° C., in particular 20 to 60° C., and subsequently an analysis of the supernatant aqueous solution in respect of its conductivity is carried out, in order to obtain an indication of the oligomer content of the monodisperse ion-exchanger and the number of necessary washing cycles for step c);

c) the monodisperse ion-exchanger is subjected to discontinuous washing with oxygen-free, completely de-ionized water until constant residual conductivity is attained; washing is effected preferably 5 to 50 times, in particular 10 to 25 times, depending on the conductivity, whereby, after discharge of the completely de-ionized water, in each instance 0.2 to 1.5 parts by volume of completely de-ionized water, relative to the monodisperse ion-exchanger which has been moistened with water, are added, the mixture is agitated and the completely de-ionized water is discharged and the conductivity is examined at the outlet, whereby the conductivity at the end of the washing cycles is less than 100 microSiemens/cm, preferably less than 50 microSiemens/cm, in particularly preferred manner less than 20 microSiemens/cm, and behaves in constant manner from wash to wash with a variation of less than 20 microSiemens/cm, and whereby the content of dissolved oxygen in the completely de-ionized water which is employed is preferably no greater than 1 ppm, preferably no greater than 100 ppb, and whereby the content of dissolved or undissolved metallic ions in the completely de-ionized water which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

d) after the final wash the completely de-ionized water is discharged, and oxygen-free phenol is admixed to the monodisperse ion-exchanger at 50 to 90° C., in particular 60 to 80° C., whereby a volume ratio of 0.60 to 1.5 parts of monodisperse ion-exchanger which has been moistened with water to one part of phenol is preferably adjusted and whereby the content of dissolved oxygen in the phenol which is used is preferably less than 1 ppm, preferably less than 100 ppb, and whereby the content of dissolved or undissolved metallic ions in the phenol which is used is preferably no greater than 1 ppm, preferably no greater than 0.5 ppm, for Fe, Co, Ni, Mo, Cr, Cu as individual components and is preferably no greater than 10 ppm, preferably no greater than 1 ppm, for the sum of the stated metals;

e) the existing mixture is dehydrated in a continuously operated circulating apparatus containing the unit (1) and at least one distillation unit (2) for the purpose of separating phenol and water, whereby the ion-exchanger which has been moistened with water is stirred in the unit (1), preferably under an inertgas atmosphere, with phenol at 50 to 90° C., preferably 60 to 80° C., and a partial flow of phenol of up to 20% of the total volume per hour is fed out via a pipe (4) and transferred into the distillation unit (2) and a separation into phenol (bottom product) and water/phenol mixture (top product) is carried out in the distillation unit (2) and the phenol is recycled into the unit (1) via pipe (4'). The phenolic water is preferably supplied to an extraction apparatus which is present in the production process. By way of distillation unit (2), in particular a distillation column which is optionally integrated within the production process is utilised for the purpose of separating water and phenol. The top product which is separated in this individual step contains 2 to 20 wt. %, preferably 5 to 10%, phenol. The phenol that is discharged from the system by this means is replenished in the unit (1) by means of fresh phenol. The mixture is conducted through the circulating apparatus until such time as a content of residual water at the outlet of the unit (1) of preferably less than 3 vol. %, preferably less than 1 vol. %, is measured;

f) the mixture is subsequently transferred in the form of a suspension consisting of ion-exchanger resin and phenol into a suitable reaction vessel, preferably under inert conditions, the suspension of ion-exchanger resin and phenol being present in pumpable form preferably at temperatures from 50 to 80° C. and preferably with a solids content from 40 to 80 vol. % and preferably g) the supernatant phenol is discharged from the reaction vessel.

The present invention preferably provides, moreover, the monodisperse ion-exchangers that have been conditioned for the synthesis of bisphenols in accordance with process steps a) to g) in the cation form.

The monodisperse ion-exchangers that have been conditioned in the ways described above are outstandingly suitable for implementing condensation reactions, for example for producing bisphenols, in particular for producing BPA from acetone and phenol. The BPA that is produced with this conditioned monodisperse ion-exchanger exhibits high product quality and is particularly suitable for the production of polymers such as epoxy resins and, in particular, polycarbonate.

The phenol that arises in the process according to the invention in the course of the conditioning of the monodisperse ion-exchanger in the case of the synthesis of bisphenols during g) is contaminated with acidic soluble portions stemming from the ion-exchanger. For arbitrary further use, in particular as initial material for the production of BPA, the phenol arising in this way is therefore optionally purified, preferably by distillation, the bottom of the column being charged with up to 5 wt. % of a basic compound that is suitable to retain acidic constituents. A preferred basic compound is sodium hydroxide.

An advantage of the process that has been described for the production of bisphenols, in particularly preferred manner for the production of BPA, consists in the fact that, by this means, undesirable acidic oligomer portions are removed from the monodisperse ion-exchanger (resulting, for example, in improved product quality). By virtue of the catalyst pretreatment in an external container, the production process can be continued in the reaction vessel during conditioning. The continuous dehydration of the catalyst with recycling of phenol requires a minimal quantity of phenol; no additional, technically sophisticated pieces of apparatus such as, for example, devices for vacuum drying or carrier-gas drying, are necessary. By virtue of the agitation of the suspension in the course of the dehydration, no mechanical stresses occur as a result of the diminution in volume of the particles of the ion-exchanger. Bypass flows arising can be processed in a production plant in which the monodisperse ion-exchangers are employed as catalysts and in which distillation units and extraction units are present. In this connection the greater part of the phenol that is used for the purpose of dehydration can also be employed in the production process.

In FIG. 1

(1) represents a stirrer vessel
(2) represents a distillation unit
(3) represents a phenol supply pipe
(4) represents phenol circulating pipes
(5) represents water/(phenol) discharge pipe Furthermore, and this is likewise provided by the present invention, the conditioned monodisperse ion-exchangers that are produced in accordance with the conditioning process claimed in this application can be employed as catalysts for a large number of further reactions.

Thus the conditioned monodisperse ion-exchangers in the cation form or anion form are suitable as catalysts not only for condensation reactions but also for addition reactions, for example of alcohols to alkenes to form ethers, as catalysts in the case of esterifications or transesterifications but also as catalysts in the case of alkylation reactions.

For example, the conversion of methanol with isobutene or isopentene to form methyl-t-butyl ether or t-amyl methyl ether can be catalysed with the ion-exchangers in the cation form that have been conditioned in accordance with the invention.

Monodisperse ion-exchangers are preferred in accordance with the invention.

The ion-exchangers that have been conditioned in accordance with the invention are particularly suitable for the production of bisphenols, in particular BPA.

The following Examples serve to elucidate the invention. The invention is not limited to the Examples.

EXAMPLES

Example 1

Commercially available ion-exchanger (Lewatit SC 104, Bayer AG) is prepared in accordance with the scheme described above. The washing with water (oxygen content in the completely de-ionized water: 50 ppb) is undertaken under nitrogen atmosphere in 12 cycles at 30° C., the residual conductivity of the wash water at the outlet amounts in the final cycle to 14 microSiemens/cm. Dehydration is effected continuously under nitrogen atmosphere at 70° C. with 0.60 parts by volume of phenol (oxygen content 50 ppb). In the process the volume of the ion-exchanger diminishes by 40%. The hydrous phenol arising at the outlet is distilled off by distillation at, initially, 700 mbar and 105° C. bottom temperature. Towards the end of the distillation the vacuum is lowered to 130 mbar; the bottom temperature rises to 125° C. In this way, 1 to 10% of the quantity of liquid which is present overall in the stirrer vessel is passed across the distillation column per hour in increasing quantity. Phenol is recycled into the dehydration container as bottom product. The top product of the column (8% phenol, 92% water) is supplied to a continuous extraction plant. In this way, extracted phenol is continuously replenished by means of fresh phenol.

The continuous dehydration is concluded when a water content of 0.2% water in phenol is obtained at the outlet. The ion-exchanger is transferred into the reaction vessel at 70° C. as a suspension in phenol (solids content: 40 vol. %). Supernatant phenol is discharged and purified by distillation at 120° C., 150 mbar over sodium hydroxide (0.001 wt. %).

The ion-exchanger that has been prepared in this way is utilised for the continuous production of 2,2-bis(4-hydroxyphenyl)propane from a mixture of phenol (96%) and acetone (4%) at 65° C. In this process an acetone conversion of 96% and a selectivity of 93.5% BPA are achieved with a throughput of 0.15 l/l*h. The colour index at the outlet of the reactor amounts to 5 Hazen. The reaction mixture at the outlet of the reactor is subsequently tempered for 4 h at 190° C.; in the process the colour index rose from 5 Hazen to 15 Hazen.

If the reaction is carried out with the phenol that has been recovered by alkaline distillation, no measurable differences in respect of conversion, selectivity, colour index and colour development can be detected in the course of tempering.

Comparative Example 2

Preparation of the ion-exchanger is carried out in the manner described in Example 1, but the phenol that is utilised for the purpose of dehydration is subsequently utilised directly for the production of BPA without alkaline distillation. The acetone conversion amounted to 94%, the selectivity amounted to 93%, and the Hazen colour index at the outlet of the reactor amounted to 10 Hazen. This value rises after tempering (4 h at 190° C.) to 30 Hazen.

Comparative Example 3

Commercially available ion-exchanger (Lewatit SC 104, Bayer AG) is prepared in a manner analogous to Example 1 and is utilised for the production of BPA, but initial washing with water is dispensed with. An acetone conversion of 94% and a selectivity of 92.5% are observed. The Hazen colour index of the reaction mixture amounts to 15 Hazen. This value rises after 4 h at 190° C. to 40 Hazen.

Comparative Example 4

Commercially available ion-exchanger (Lewatit SC 104, Bayer AG) is prepared in a manner analogous to Example 1 and is utilised for the production of BPA, but in the course of the dehydration with phenol a water value of 10% in the outflowing phenol is obtained at the end. An acetone conversion of 86% and a selectivity of 93.0% are observed. The Hazen colour index of the reaction mixture amounts to 10 Hazen. This value rises after tempering (4 h at 190° C.) to 25 Hazen.

Comparative Example 5

Commercially available ion-exchanger (Lewatit SC 104, Bayer AG) was prepared in a manner analogous to Example 1 and was utilised for the production of BPA, but an intensive operation for rendering it inert in the course of washing with water was dispensed with. In addition, the completely de-ionized water that was used for the washing contained 2 ppm dissolved oxygen, 5 ppm Fe, 2 ppm Co and 2 ppm Ni. An acetone conversion of 93% and a selectivity of 93.0% were observed. The Hazen colour index of the reaction mixture amounted to 15 Hazen. This value rose after tempering (4 h at 190° C.) to 30 Hazen.

Example 6

Condensation reaction exemplified by the synthesis of bisphenols, here BPA:

Commercially available monodisperse ion-exchanger (Lewatit K 1261®, Bayer AG) is prepared in accordance with the scheme described above. The washing with water (oxygen content in the completely de-ionized water: 50 ppb) is undertaken under nitrogen atmosphere in 12 cycles at 30° C., the residual conductivity of the wash water at the outlet amounts in the final cycle to 14 microSiemens/cm. Dehydration is effected continuously under nitrogen atmosphere at 70° C. with 0.60 parts by volume of phenol (oxygen content 50 ppb). In the process the volume of the monodisperse ion-exchanger diminishes by 40%. The hydrous phenol arising at the outlet is distilled off by distillation at, initially, 700 mbar and 105° C. bottom temperature. Towards the end of the distillation the vacuum is lowered to 130 mbar, the bottom temperature rises to 125° C. In this way, 1 to 10% of the quantity of liquid which is present overall in the stirrer vessel is passed across the distillation column per hour in increasing quantity. Phenol is recycled into the dehydration container as bottom product. The top product of the column (8% phenol, 92% water) is supplied to a continuous extraction plant. In this way, extracted phenol is continuously replenished by means of fresh phenol.

The continuous dehydration is concluded when a water content of 0.2% water in phenol is obtained at the outlet. The monodisperse ion-exchanger is transferred into the reaction vessel at 70° C. as a suspension in phenol (solids content: 40 vol. %). Supernatant phenol is discharged and purified by distillation at 120° C., 150 mbar over sodium hydroxide (0.001 wt. %).

The ion-exchanger that has been prepared in this way is utilised for the continuous production of 2,2-bis(4-hydroxyphenyl)propane from a mixture of phenol (96%) and acetone (4%) at 65° C. In this process an acetone conversion of 96% and a selectivity of 93.5% BPA are achieved with a throughput of 0.15 l/l*h. The colour index at the outlet of the reactor amounts to 5 Hazen. The reaction mixture at the outlet of the reactor is subsequently tempered for 4 h at 190° C.; in the process the colour index rose from 5 Hazen to 15 Hazen.

If the reaction is carried out with the phenol that has been recovered by alkaline distillation, no measurable difference in respect of conversion, selectivity, colour index and colour development can be detected in the course of tempering.

Comparative Example 7

Commercially available heterodisperse ion-exchanger (Lewatit SC 104®, Bayer AG) is prepared in a manner analogous to Example 1 and is utilised for the production of BPA, but initial washing with water is dispensed with. An acetone conversion of 94% and a selectivity of 92.5% are observed. The Hazen colour index of the reaction mixture amounts to 15 Hazen. This value rises after 4 h at 190° C. to 40 Hazen.

What is claimed is:

1. A process for conditioning monodisperse ion-exchangers for the catalysis of condensation reactions, addition reactions, transesterifications, esterifications or alkylation reactions, comprising the steps of
    a) moistening monodisperse ion-exchangers with water,
    b) suspending the moistened ion-exchangers in oxygen-free completely de-ionized water,
    c) washing the suspended ion-exchanger with oxygen-free completely deionized water until constant conductivity is attained,
    d) after washing, discharging the completely de-ionized water,
    e) admixing an oxygen-free OH component to the monodisperse ion-exchanger,
    f) dehydrating the mixture in a continuously operated circulating apparatus with a distillation unit, and
    g) transferring the suspension comprising the monodisperse ion-exchanger and OH component into a reaction vessel.

2. A process for conditioning ion-exchangers, comprising the steps of
    a) moistening the ion-exchanger with water,
    b) suspending the moistened ion-exchanger in a unit with oxygen-free, completely de-ionized water at about 5 to about 80° C.,
    c) agitating the suspension,
    d) discontinuously washing the ion-exchanger with oxygen-free, completely de-ionized water until constant residual conductivity is attained,
    e) after washing, discharging the completely de-ionized water,
    f) admixing oxygen-free phenol to the ion-exchanger at temperatures from about 50 to about 90° C. to form a mixture,
    g) dehydrating the mixture in a continuously operated circulating apparatus containing the unit and at least one distillation unit for the purpose of separating phenol and water,
    h) transferring the ion-exchanger/phenol suspension into a reaction vessel.

3. Process according to claim 2, wherein the ion-exchanger is a monodisperse ion-exchanger.

4. Process according to claim 3, wherein after the ion-exchanger/phenol suspension has been transferred into the reaction vessel supernatant phenol is discharged.

5. Process according to claim 1, wherein the monodisperse ion-exchangers have a gel-like or macroporous structure.

6. Process according to claim 2, wherein the content of dissolved or undissolved metallic ions in the completely de-ionized water is no greater than 1 ppm for Fe, Co, Ni, Mo, Cr, Cu.

7. Process according to claim 6, wherein the content of dissolved or undissolved metallic ions is no greater than 10 ppm for the sum of the stated metals.

8. Process according to claim 2, wherein after the ion-exchanger/phenol suspension has been transferred into the reaction vessel the supernatant phenol is discharged.

* * * * *